(12) United States Patent
Valleri et al.

(10) Patent No.: US 7,067,154 B1
(45) Date of Patent: Jun. 27, 2006

(54) PHARMACEUTICAL COMPOSITIONS CONTAINING VITAMIN D AND CALCIUM, THEIR PREPARATION AND THERAPEUTIC USE

(75) Inventors: Maurizio Valleri, Florence (IT); Alessandro Tosetti, Bagno a Ripoli (IT)

(73) Assignee: Menarini International Operations Luxembourg S.A., Luxembourg ( * ) Notice: Subject to any disclaimer, the term of this patent is extended or adjusted under 35 U.S.C. 154(b) by 0 days.

(21) Appl. No.: 09/463,586

(22) PCT Filed: Jul. 21, 1998

(86) PCT No.: PCT/EP98/04567

§ 371 (c)(1),
(2), (4) Date: Apr. 24, 2000

(87) PCT Pub. No.: WO99/06051

PCT Pub. Date: Feb. 11, 1999

(30) Foreign Application Priority Data

Jul. 30, 1997 (IT) ................................ FI97A0184

(51) Int. Cl.
*A61K 9/16* (2006.01)
*A61K 9/20* (2006.01)

(52) U.S. Cl. .................... 424/501; 424/489; 424/464; 424/470; 424/602

(58) Field of Classification Search ........ 424/489–502, 424/602, 678, 687, 464, 469, 470; 514/171
See application file for complete search history.

(56) References Cited

U.S. PATENT DOCUMENTS 4,493,822 A * 1/1985 Tovey ..................... 424/464
5,576,021 A * 11/1996 Andoh et al. ............. 424/465

FOREIGN PATENT DOCUMENTS

| EP | 0588539 | 3/1994 |
| FR | 2073271 | 10/1971 |
| FR | 2724844 | 9/1994 |
| WO | 9609036 | 3/1996 |

OTHER PUBLICATIONS

Remington's Pharmaceutical Sciences, Eighteenth Edition, Mack Publishing Company, Easton, Pennsylvania, 1990: pp. 1635-1636.*

* cited by examiner

*Primary Examiner*—Gollamudi S. Kishore
(74) *Attorney, Agent, or Firm*—James V. Costigan; Hedman & Costigan P.C.

(57) ABSTRACT

Described herein is a pharmaceutical composition containing Vitamin D and calcium, comprising a binding agent chosen from among the group consisting of: propylene glycol, a polyethylene glycol presenting a molecular weight comprised between 300 and 1500, liquid paraffin or silicone oil, useful for the treatment of nutritional deficiency of calcium and Vitamin D in the elderly.

12 Claims, No Drawings

PHARMACEUTICAL COMPOSITIONS CONTAINING VITAMIN D AND CALCIUM, THEIR PREPARATION AND THERAPEUTIC USE

SCOPE OF THE INVENTION

The present invention refers to pharmaceutical compositions containing Vitamin D and a calcium salt, the process for their preparation, and their use in the treatment of pathological forms involving loss of bone tissue in the elderly, such as osteoporosis, as well as in the prevention of illnesses linked to calcium metabolism in the elderly, such as those leading to fractures of the proximal femur or other non-vertebral fractures.

STATE OF THE ART

The use of Vitamin D and calcium salts, either separately or in association, for various illnesses, among which those concerning calcium metabolism in the elderly, is already well documented in the state of the art. For example, in FR 2724844, the existence of a therapeutic association is claimed between Vitamin D and calcium salts in combating osteoporosis.

However, the Vitamin D and calcium-based pharmaceutical formulations available today still present a number of problems which render them not altogether acceptable.

The problems that had to be faced for the pharmaceutical compositions that are the subject of the present invention were in particular:

a) the homogeneity of distribution of Vitamin $D_3$ in the final mixture;

b) the properties of flow of the powder of the calcium salt used; and, when present, c) the rate of reconstitution of the suspension to be prepared as and when required.

In fact, for the preparation of these formulations, normally Vitamin D is used in the so-called "coated" form, since it presents greater stability than the pure crystalline form.

The "coated" form, however, presents the disadvantage of consisting of small granules that are highly dense and smooth, which renders their distribution inside the final mixture even more problematic, this distribution in itself already being complex on account of the small amount of the vitamin involved in comparison with the other constituents of the pharmaceutical compositions that are the subject of the present patent.

In addition, the calcium salt used for this type of preparations normally undergoes a granulation process (either damp or dry) to overcome the problems due to the poor characteristics of flow that it presents in its most widely used form, i.e., in the form of fine powder, which makes it unsuitable for processing using ordinary high output rate machines. However, the granules (including those obtained with specific excipients for favouring disgregation) present a poor disgregation rate, which is instead highly desirable for the pharmaceutical preparation in bags, both in order to guarantee a good level of bio-availability and to obtain a suspension to be prepared as and when required, in which the salt may be finely divided in order to reduce the rate of sedimentation of the suspension and eliminate the "sand" effect which is noted when granular suspensions of this type are taken.

There is therefore an evident need to have available new pharmaceutical formulations containing a Vitamin D-calcium association which may enable a high dosage of calcium mixed in a homogenous way with very low doses of Vitamin D (for example 1–2 g of calcium for 500–1000 I.U. of Vitamin D), may present a good stability, may have a high level of bio-availability, may be suited to being processed using high-speed production machines, and may be pleasant to take for the patient.

DETAILED DESCRIPTION OF THE INVENTION

The pharmaceutical composition according to the invention makes it possible to overcome the aforesaid problems owing to a "granulation" of the calcium salt, at the rate of 1–2 g of calcium for 500–1000 I.U. of vitamin D, in the presence of propylene glycol or a polyethylene glycol presenting a molecular weight comprised between 300 and 1500 (for formulations that involve subsequent disgregation in water) or (in the case of pharmaceutical formulations that do not envisage subsequent disgregation) with liquid paraffin or silicone oil.

Surprisingly, the addition of the calcium salt to the above said glycols makes it possible to obtain, a triple advantageous effect:

a) The even and diffused distribution of the glycol over the calcium granules, as well as over the other components of the formulation, plays a "binding" effect on the small granules of coated Vitamin $D_3$. In this way, there is an anchoring of the particles of the vitamin to the system, thus enabling its even distribution;

b) The atypical granulation of the calcium salt, taking place with this agent, modifies the properties of flow just enough to obtain a mixture having characteristics of smoothness such as to enable its processing with high output machines;

c) The aforesaid modification of the properties of flow of the calcium salt however is not an obstacle to its complete re-dispersion, where this is required, once the aqueous suspension has been reconstituted.

Moreover the moistening effect exerted by the propylene glycol on the calcium phosphate must be considered. This effect renders the operation of reconstitution of a dispersion faster than the one obtainable without its use.

According to the invention particularly preferred is propylene glycol. In this connection it is important to note that the well-known sour taste of propylene glycol or somewhat bitter one of low-molecular-weight polyethylene glycols may be easily covered by the common excipients and sweeteners, without affecting the pleasantness of the resultant pharmaceutical composition.

As binding agents for pharmaceutical forms that do not have to be dispersed in water, the substances that have proved extremely useful, and hence constitute a subject of the present invention, are liquid paraffin and silicone oil. These components in fact make it possible to obtain the same aggregating effect as the previous excipients and an equivalent distribution of the active principles.

Among the various forms of Vitamin D used for the formulations according to the invention, Vitamin $D_3$, Vitamin $D_2$ and their mixtures are preferred.

The calcium salt used for the present invention is, for example, chosen in the group consisting of: phosphate, glycerophosphate, carbonate, bicarbonate, lactate, citrate, tartrate, gluconate, and chloride.

Particularly preferred is calcium phosphate and, more particularly, tribasic phosphate.

Normally the quantity of calcium phosphate is comprised between 30–80% by weight calculated on the total composition.

The pharmaceutical compositions that form the subject of the present patent moreover comprise the usual moistening agents (e.g., sucrose palmitate); fluidifying agents (such as, colloidal silica); suspending agents (such as cellulose, carboxymethyl cellulose, sodium carboxymethyl cellulose); organoleptic correctors (such as, flavouring substances, citric acid); sweeteners (such as mannitol, sorbitol, saccharin salts, aspartame, etc.); and colouring agents (such as E110). It must be noted that the pharmaceutical compositions according to the present invention are not suitable for dermatology applications (for example in the form of creams).

According to a preferred formulation (bags) the pharmaceutical composition of the present application contains the propylene or the polyethylene glycol in a quantity comprised between 5–15% by weight calculated on the total weight of the formulation.

Non-limiting examples of the present invention are the following:

EXAMPLE 1

Lot for 6000 bags

The sucrose palmitate, citric acid and sodium saccharin are sifted using a sieve with 0.5-mm mesh.

The propylene glycol is distributed over the calcium phosphate in a high speed granulator by setting the following process parameters:

2 minutes with impeller at 80 r.p.m. and chopper turned off, followed by 2 minutes with impeller at 160 r.p.m. and chopper at 1500 r.p.m.

The colloidal silica, 25% of the mannite required, the citric acid, and the sodium saccharin are added to the mixture.

The above is mixed for 6 minutes with impeller at 80 r.p.m. and chopper at 1500 r.p.m. until a homogeneous composition is obtained.

Prepared separately, in a cube mixer at a rate of 25 r.p.m. for 15 minutes, is a premix consisting of sucrose palmitate, microcrystalline cellulose and carboxymethyl cellulose, lemon flavouring, E110, the remaining part of the mannite, and the Vitamin $D_3$.

The mixture thus obtained is transferred into the granulator and mixed with the rest of the preparation, according to the following parameters:

1 minute with impeller at 140 r.p.m. and chopper at 1500 r.p.m., followed by 30 seconds with impeller at 140 r.p.m. and chopper turned off.

The granulate thus obtained is distributed in the bags, which thus contain a preparation having the following composition:

| | |
|---|---|
| Tribasic calcium phosphate (corresponding to 1200 mg of $Ca^{++}$) | 3.100 g |
| Cholecalciferol (Vit. $D_3$) 100 000 IU/g (corresponding to 800 IU) | 0.008 g |
| Propylene glycol | 0.800 g |
| E110 | 0.002 g |
| Colloidal silica | 0.120 g |
| Lemon flavouring | 0.100 g |
| Microcrystalline cellulose - MCC | 0.200 g |
| Sodium saccharin | 0.015 g |
| Anhydrous citric acid | 0.165 g |
| Sucrose monopalmitate | 0.120 g |
| Mannitol q.s. to | 7.000 g |

In a similar way, but using polyethylene glycol instead of propylene glycol, bags may be prepared containing a preparation having the following composition:

| | |
|---|---|
| Tribasic calcium phosphate (corresponding to 1200 mg of $Ca^{++}$) | 3.100 g |
| Cholecalciferol (Vit. $D_3$) 100 000 IU/g (corresponding to 800 IU) | 0.008 g |
| Polyethylene glycol 400 | 0.800 g |
| E110 | 0.002 g |
| Colloidal silica | 0.120 g |
| Lemon flavouring | 0.100 g |
| Microcrystalline cellulose - MCC | 0.200 g |
| Sodium saccharin | 0.015 g |
| Anhydrous citric acid | 0.165 g |
| Sucrose monopalmitate | 0.120 g |
| Mannitol q.s. to | 7.000 g |

EXAMPLE 2 (tablets)

Preparation for 20,000 tablets

The liquid paraffin is distributed over the calcium phosphate in a high speed granulator, setting the following process parameters:

2 minutes with impeller at 80 r.p.m. and chopper turned off, followed by 2 minutes with impeller at 160 r.p.m. and chopper at 1500 r.p.m.

The colloidal silica, the carboxymethyl cellulose, the sodium saccharin and the orange flavouring are sifted using a sieve with a 0.5-mm mesh.

Vitamin $D_3$ is added to the above-mentioned components and the product is mixed using a cube mixer at a rate of 25 r.p.m. for 5 minutes.

The sorbitol is then added, and everything is mixed in the cube mixer for 10 minutes at 25 r.p.m.

This premix is transferred into the granulator and is mixed with the rest of the preparation, by setting the following process parameters:

1 minute with impeller at 140 r.p.m. and chopper at 1500 r.p.m., followed by 30 seconds with impeller at 140 r.p.m. and chopper turned off.

The granulate is compressed to the required weight to obtain tablets having the following composition:

| | |
|---|---|
| Tribasic calcium phosphate (corresponding to 1200 mg of $Ca^{++}$) | 3.100 g |
| Cholecalciferol (Vit. $D_3$) 100 000 IU/g (corresponding to 800 IU) | 0.008 g |
| Liquid paraffin | 0.500 g |
| Sodium carboxymethyl cellulose | 0.050 g |
| Sodium saccharin | 0.015 g |
| Orange flavouring | 0.100 g |
| Sorbitol q.s. to | 4.400 g |

In the same way, using silicone oil instead of liquid paraffin, it is possible to obtain tablets having the following composition:

| | |
|---|---|
| Tribasic calcium phosphate (corresponding to 1200 mg of Ca$^{++}$) | 3.100 g |
| Cholecalciferol (Vit. D$_3$) 100 000 IU/g (corresponding to 800 IU) | 0.008 g |
| Silicone oil | 0.500 g |
| Sodium carboxymethyl cellulose | 0.050 g |
| Sodium saccharin | 0.015 g |
| Orange flavouring | 0.100 g |
| Sorbitol q.s. to | 4.400 g |

The pharmaceutical compositions that form the subject of the present invention were made for the purpose of being used in the treatment of nutritional deficiency of calcium and Vitamin D in the elderly, to reduce the loss of bone tissue linked to age and to prevent proximal femur fractures and other non-vertebral fractures. These pharmaceutical compositions may be used also to prevent osteoporosis induced by chronic treatment with corticosteroids.

I.U. as used in the present application means International Units and corresponds to the amount having the activity of 0.0025 γ of Vitamin D$_3$.

The invention claimed is:

1. A granular pharmaceutical composition which consists essentially of Vitamin D and calcium phosphate, as active principles and a binding agent selected from the group consisting of propylene glycol, a polyethylene glycol of molecular weight between 300 and 400; liquid paraffin and silicone oil, said Vitamin D being present in an amount of 500–1000 I.U. of Vitamin D and said calcium salt being present in a ratio of 1–2 g of calcium, calculated as elemental calcium, for each 500–1000 I.U. of Vitamin D.

2. Pharmaceutical composition according to claim 1, wherein the calcium phosphate is 30–80% by weight calculated on the total composition.

3. Pharmaceutical composition according to claim 1, in which the Vitamin D used is Vitamin D$_2$, Vitamin D$_3$, or one of their mixtures.

4. Pharmaceutical composition according to claim 3, in which the vitamin D used is Vitamin D$_3$.

5. A granular pharmaceutical composition in a sachet dosage form according to claim 1, containing propylene glycol or polyethylene glycol of molecular weight between 300 and 400 in a quantity comprised between 5–15% by weight calculated on the total composition in a sachet.

6. A granular pharmaceutical composition according to claim 1, wherein the binder is liquid paraffin or silicone oil.

7. A pharmaceutical composition in a tablet dosage form which consists essentially of:

| | |
|---|---|
| Tribasic calcium phosphate (corresponding to 1200 mg of Ca$^{++}$) | 3.100 g |
| Cholecalciferol (Vit. D$_3$) 100,000 IU/g (corresponding to 800 IU) | 0.008 g |
| Liquid paraffin | 0.500 g |
| Sodium carboxymethyl cellulose | 0.050 g |
| Sodium saccharin | 0.015 g |
| Orange flavoring | 0.100 g |
| Sorbitol q.s. to | 4.400 g. |

8. A pharmaceutical composition in a tablet dosage form which consists essentially of:

| | |
|---|---|
| Tribasic calcium phosphate (corresponding to 1200 mg of Ca$^{++}$) | 3.100 g |
| Cholecalciferol (Vit. D$_3$) 100,000 IU/g (corresponding to 800 IU) | 0.008 g |
| Silicone oil | 0.500 g |
| Sodium carboxymethyl cellulose | 0.050 g |
| Sodium saccharin | 0.015 g |
| Orange flavoring | 0.100 g |
| Sorbitol q.s. to | 4.400 g. |

9. Method for treatment of nutritional deficiency of calcium and Vitamin D in the elderly, to reduce the loss of bone tissue linked to age and to prevent femoral fractures and other non-vertebral fractures, in which therapeutically effective quantities of a composition according to claim 1 are administered to the patient.

10. Method according to claim 9 for the prevention of osteoporosis induced by treatment with corticosteroids.

11. A granular pharmaceutical composition as defined in claim 1 wherein the binder is polyethylene glycol having a molecular weight of 400 and the granular pharmaceutical composition is in a sachet.

12. A granular pharmaceutical composition as defined in claim 1 wherein the binder is propylene glycol and the granular pharmaceutical composition is in a sachet.

\* \* \* \* \*